(12) United States Patent
High et al.

(10) Patent No.: US 8,063,022 B1
(45) Date of Patent: Nov. 22, 2011

(54) METHODS FOR PREVENTING FORMATION OF INHIBITORY ANTIBODIES IN THE SETTING OF GENE THERAPY

(75) Inventors: Katherine A. High, Merion, PA (US); Paul A. Fields, Philadelphia, PA (US); Valder R. Arruda, Philadelphia, PA (US); Roland W. Herzog, Glenolden, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/589,589

(22) Filed: Jun. 8, 2000

Related U.S. Application Data

(60) Provisional application No. 60/138,066, filed on Jun. 8, 1999.

(51) Int. Cl.
*A61K 48/00* (2006.01)
*A61K 47/00* (2006.01)

(52) U.S. Cl. .................................. 514/44 R; 424/278.1

(58) Field of Classification Search ............... 435/320.1, 435/456, 457, 455; 424/93.2, 93, 6, 184.1, 424/278.1, 93.21; 536/23.1; 514/44, 44 R
See application file for complete search history.

(56) References Cited

U.S. PATENT DOCUMENTS

| | | | |
|---|---|---|---|
| 5,698,443 A | 12/1997 | Henderson et al. | |
| 5,952,221 A | 9/1999 | Kurtzman et al. | |
| 6,071,883 A | 6/2000 | Chen et al. | |
| 6,093,392 A | 7/2000 | High et al. | |
| 6,093,567 A | 7/2000 | Gregory et al. | |
| 6,251,957 B1 * | 6/2001 | Wilson et al. ................ | 424/85.2 |
| 6,929,796 B1 * | 8/2005 | Conti-Fine ................ | 424/185.1 |
| 2003/0004091 A1 * | 1/2003 | Perricaudet et al. ............... | 514/1 |
| 2003/0130221 A1 * | 7/2003 | High et al. ...................... | 514/44 |
| 2003/0134815 A1 * | 7/2003 | Crystal ........................... | 514/44 |

FOREIGN PATENT DOCUMENTS

| WO | WO 96/25177 | * 8/1996 |
|---|---|---|
| WO | WO 97/39776 | * 10/1997 |

OTHER PUBLICATIONS

Potter et al., Review- The use of immunosuppressive agents to prevent neutralizing antibodies against a transgene product,1999, Ann. NY Acad. Sci., vol. 875, pp. 159-174.*
Verma et al, Gene therapy-promises, problems and prospects, 1997, Nature, vol. 389, pp. 239-242.*
Anderson, Human gene therapy, 1998, Nature, vol. 392, pp. 25-30.*
Smith et al., Transient immunosuppression permits successful repetitive intravenous administration of an adenovirus vevtor, 1996, Gene Therapy, vol. 3, pp. 496-502.*
Kay et al., Evidence for gene transfer and expression of factor IX in haemophilia B patients treated with an AAV vector, 2000, Nature Genetics, vol. 24, pp. 257-261.*
Jooss et al., Cyclophosphamide diminishes inflammation and prolongs transgene expression following delivery of adenoviral vectors to mouse liver and lung, 1996, Human Gene Therapy, vol. 7, pp. 1555-1566.*
Fang et al., Gene therapy for hemophilia B: Host immunosuppression prolongs the therapeutic effect of adenovirus-mediated factor IX expression, 1995, Human Gene Therapy, vol. 6, pp. 1039-1044.*
Rubanyi, The future of human gene therapy, 20001, Molecular Aspects of Medicine, vol. 22, pp. 113-142.*
RW Herzog et al., Molecular Therapy, "Muscle-Directed Gene Transfer and Transient Immune Suppression Result in . . . Hemophilia B Caused by a Null Mutation," Sep. 2001, vol. 4, No. 3, pp. 192-200.*
Warrier et al., Blood Caput Fibrinolysis Mar. 1998: 9 Suppl 1: S125-8.*
Nilsson, PNAS, 83:9169-9173, 1986.*
Herzog et al., Blood 1997, vol. 90, No. 10, Part 1, Suppl [1], pp. 1057-1057.*
Tripathy, Nat. Med. 1996, vol. 2, pp. 545-550.*
Chirmule et al. Gene Therapy, 6, pp. 1574-1583, 1999.*
Xiao et al. Molecular Therapy, 1, pp. 323-329, 2000.*
Arruda et al Blood. May 1, 2005;105(9):3458-64).*
Ecke, Goodman & Gilman's The Pharmacological basis of Therapeutics, 1996, McGraw-Hill, New York, NY. pp. 77-101.*
Arruda et al Blood, 2004, 103(1) 85-92.*
Manno et al Nature Medicine, 2006, 12(3), 342-347.*
Gautam et al Am J Respir Med, 2002;1(1):35-46.*
Ponder et al Current Opinion Hematol, 2006, 13, 301-307.*
Kaiser Science, 317, 2007, 580.*
Chao et al The Mount Sinai J of Medicine, 71(5), 2004, 305-312.*
Walsh Gene Therapy, 2003, 10, 999-1003 .*
Herzog et al, Human Gene therapy, 13:1281-1291 2002.*
Matthew et al Journal of Clinical Investigation, 1987, 79, 746-753.*
Cater, 1992, "Adeno-associated Virus Vectors," Biotechnology, 3: 533-539.
Dai, et al., 1995 "Cellular and Humoral Immune Responses to Adenoviral Vectors Containing Factor IX Gene: Tolerization of Factor IX and Vector Antigens Allows for Long-term Expression," Proc. Natl. Acad. Sci. USA, 92:1401-1405.
High, et al., 1995, "Factor IX In: Molecular Basis of Thrombosis and Hemostasis," High and Roberts, (eds.), Marcel Dekker, Inc.
Herzog, et al., 1997, "Stable Gene Transfer and Expression of Human Blood Coagulation Factor IX After Intramusular Injection of Recombinant Adeno-associated Virus," Proc. Natl. Acad. Sci. USA, 94:5804-5809.

(Continued)

*Primary Examiner* — Anoop Singh
(74) *Attorney, Agent, or Firm* — Dann, Dorfman, Herrell & Skillman; Kathleen D. Rigaut

(57) ABSTRACT

The invention provides a method of preventing the formation of inhibitory antibodies in a mammal undergoing gene therapy. The method comprises administering to the mammal an immunosuppressive agent in conjunction with the gene therapy.

4 Claims, 3 Drawing Sheets

OTHER PUBLICATIONS

Herzog, et al., 1999, "Long-term Correction of Canine Hemophilia B by Gene Transfer of Blood Coagulation Factor IX Mediated by Adeno-associated Viral Vector,"Nature Medicine, 5:56-63.

Herzog and High, 1999, "Adeno-associated Vrius-mediated Gene Transfer of Factor IX for Treatment of Hemophilia B by Gene Therapy," In: Thrombosis and Hemostasis, 1999 State of the Art, Hoyer L(ed.), 82:540-546.

Kaplitt, et al., 1994, Long-term Gene Expression and Phenotypic Correction Using Adeno-associated Virus Vectors in the Mammalian Brain, Nature Genetics, 8:148-154.

Kay, et al., 1993, "In Vivo Gene Therapy of Hemophilia B: Sustained Partial Correction in Factor IX-Deficient Dogs," Science, 262:117-119.

Kay, et al., 1997,"Transient Immunomodulation with Anti-CD40 Ligand Antibody and CTLA41g Enhances Persistence and Secondary Adenovirus-mediated Gene Transfer Into Mouse Liver," Proc. Natl. Acad. Sci. USA, 94:4686-4691.

Kessler, et al., "Gene Delivery to Skeletal Muscle Results in Sustained Expression and Systemic Delivery of a Therapeutic Protein," Proc. Natl. Acad. Sci. USA, 93: 14082-14087.

Matsushita, et al., 1998, "Adeno-associated Virus Vectors can be Efficiently Produced without Helper Virus," Gene Therapy, 5:938-945.

Matsushita, et al.,1999, Proceedings of the $2^{nd}$ Annual American Society of Gene Theraphy, Washington, DC, Jun. 9-13, p. 2a.

Nakai, et al., 1998, "Adeno-associated Viral Vector-mediated Gene Transfer of Human Blood Coagulation Factor IX Into Mouse Liver," Blood, 91: 4600-4607.

Skulimowski, et al., 1995, "Adeno-associated Virus: Integrating Vectors for Human Gene Therapy," Methods in Molecular Genetics 7:7-12.

Tripathy, et al., 1996, "Immune Responses to Transgene-encoded Proteins Limit the Stability of Gene Expression after Injection of Replication-defective Adenovirus Vectors," Nature Medicine, 2:545-550.

Tripathy, et al., 1996, "Long -term Expression of Erythropoietin in the Systemic Circloation of Mice after Intramuscular Injection of a Plasmid DNA Vector," Proc. Natl. Acad. Sci. USA, 93:10876-10880.

Xiao, et al., Efficient Long-term Gene Transfer into Muscle Tissue of Immunocompetent Mice by Adeno-associated Virus Vector, Journal of Virology, 70:8098-8108.

Yang, et al., 1996 "Immunology of Gene Therapy with Adenoviral Vectors in Mouse Skeletal Muscle," Human Molecular Genetics, 5:1703-1712.

Herzog, R.W., et al., Long-Term Correction of Canine Hemophilia B by Gene Transfer of Blood Coagulation Factor IX Mediated by Adeno-Associated Viral Vector, Nature Medicine, 5(1):56-63 (1999).

Snyder, R. O., Correction of Hemophilia B in Canine and Murine Models Using Recombinant Adeno-Associated Viral Vectors, Nature Medicine, 5(1):64-70 (1999).

* cited by examiner

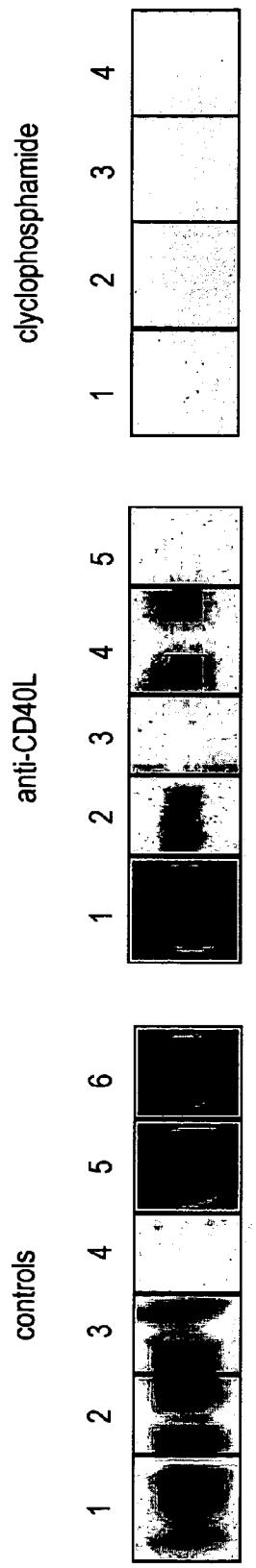
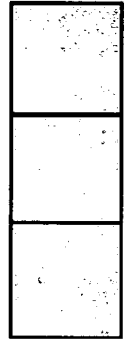
cyclophosphamide:
FIG. 4A controls (1 month)
FIG. 4B anti-CD40L (1 month)
FIG. 4C cyclophosphamide (1 month)
FIG. 4D (4 months)
FIG. 4E (5 months)

METHODS FOR PREVENTING FORMATION OF INHIBITORY ANTIBODIES IN THE SETTING OF GENE THERAPY

CROSS-REFERENCE TO RELATED APPLICATIONS

This application claims priority under 35 U.S.C. §119(e) to U.S. Provisional Application No. 60/138,066, filed on Jun. 8, 1999.

STATEMENT OF FEDERALLY SPONSORED RESEARCH AND DEVELOPMENT

This invention was made in part using funds obtained from the U.S. Government (National Institutes of Health Grant No. R01 HL61921) and the U.S. Government may therefore have certain rights in the invention.

BACKGROUND OF THE INVENTION

The process of blood coagulation involves a series of proteins known as blood coagulation proteins which act in a cascade fashion to effect the formation of a blood clot. Hemophilia is a disease of humans and other mammals wherein a gene encoding a blood coagulation factor contains a mutation such that the encoded protein does not function normally in the cascade process. Specifically, the hereditary disease, hemophilia B, is characterized by a mutation in the gene encoding the blood coagulation protein, Factor IX (F.IX). F.IX is reviewed in High et al. (1995, "Factor IX" In: Molecular Basis of Thrombosis and Hemostasis, High and Roberts, eds., Marcel Dekker, Inc.).

Adenoviral vectors are well known in gene therapy and have been used to effect expression of high levels of canine factor IX in immunodeficient mice or in immunocompetent mice when the virus is administered in conjunction with immunosuppressive agents. When adenoviral vectors are administered to immunocompetent mice in the absence of immunosuppressive agents, these vectors induce a strong inflammatory and cytotoxic T lymphocyte (CTL) response (Dai et al., 1995, Proc. Natl. Acad. Sci. USA 92:1401-1405) which negates the beneficial effects of the therapy. In addition, there are reports which suggest that intramuscular injection of replication defective adenovirus provides long-term expression of a transgene, provided that the transgene encodes a self-protein (i.e., a host protein), such that a strong host immune response is avoided (Tripathy et al., 1996, Nature Med. 2:545-550; Yang et al., 1996, Hum. Mol. Genet. 5:1703-1712). Thus, while there has been significant progress in the area of gene therapy in in vivo expression of a selected transgene following direct injection of an adenoviral vector into skeletal muscle, the use of adenoviral vectors may not be the optimal method for gene therapy in light of these immunological considerations.

Retroviral vectors have also been used experimentally as a model for treatment of hemophilia B. However, levels of expression of F.IX from these vectors are reported to be too low to be of therapeutic value (Kay et al., 1993, Science 262:117-119).

Plasmid DNA which has been injected into mouse muscle has been shown to direct expression of erythropoietin (Epo) (Tripathy et al., 1996, Proc. Natl. Acad. Sci. USA 93:10876-10880), but this method of gene therapy is apparently not sufficiently efficient for the expression of a gene product such as F.IX, which is needed at relatively high levels in the circulation (compared with Epo) to achieve a therapeutic effect.

Adeno-associated virus (AAV) is an alternative vehicle to adenovirus for delivery of genes to muscle. Recombinant AAV (rAAV) does not contain sequences encoding viral proteins and has the potential to integrate into the chromosomal DNA of the host cell (Carter, 1992, Curr. Opin. Biotech. 3:533-539; Skulimowski et al., 1995, Method Mol. Genet. 7:7-12). Production and purification procedures are now available which facilitate the generation of pure rAAV which is not contaminated by wild-type AAV or helper adenovirus. As noted herein, administration of adenovirus to mammals is accompanied by the aforementioned immunological problems.

While the efficiency of in vivo transduction with rAAV in the absence of helper virus is low for some cell types, certain post-mitotic cells such as neurons (Kaplitt et al., 1994, Nature Genet. 8:148-154) and skeletal muscle fibers (Xiao et al., J. Virol. 70:8098-8108) can be effectively transduced with this vector. Stable expression of lacZ for up to 1.5 years has been reported (Xiao et al., supra). In contrast to adenoviral vectors, intramuscular injection with rAAV in immunocompetent animals does not result in a CTL response against transduced muscle fibers, nor are circulating antibodies against the intracellular lacZ gene product present.

The results of Southern blot hybridization and PCR analyses of genomic DNA obtained from skeletal muscle injected with rAAV establish that rAAV genomes persist in the form of tandem repeats which may be integrated into chromosomal DNA (Xiao et al., supra). The expression of the secreted protein, Epo, following intramuscular injection with rAAV is reported in Kessler et al. (1996, Proc. Natl. Acad. Sci. USA 93:14082-14087). However, the levels of protein expression reported were one to two orders of magnitude below that required for a therapeutic effect mediated by F.IX.

Current therapy for hemophilia involves the intravenous injection of a preparation of clotting factor concentrates whenever a bleed occurs. This treatment is cumbersome, inconvenient and very expensive. The average patient pays approximately $100,000 per year for the concentrate alone. Further, because the concentrate is only administered to the patient intermittently, patients remain at risk for life-threatening bleeds which are fatal if treatment is not timely administered.

In a gene therapy based setting, the production of a secretable protein in a host animal, wherein there is no endogenous expression of the gene in the host animal, may lead to an immune response to the secreted gene. While a successful regimen of gene therapy has been disclosed in International Application PCT/US98/04790, there is a need for the development of improvements to the procedures described therein. Further, there is a long felt and acute need for improved methods of delivering F.IX to mammals, in particular, to humans, having hemophilia such that a therapeutic effect is achieved. The present invention satisfies this need.

SUMMARY OF THE INVENTION

The invention relates to a method of preventing the formation of inhibitory antibodies in a mammal undergoing gene therapy. The method comprises administering to the mammal an immunosuppressive agent in conjunction with the gene therapy.

In one aspect, the mammal is a human.

In another aspect, the gene therapy is delivery of a nucleic acid to the mammal, which when expressed in the mammal, serves to correct a genetic defect in the mammal.

In yet another aspect, the protein is selected from the group consisting of Factor VII, Factor VIII, Factor IX, Factor X, alpha1-antitrypsinogen, glucuronidase, a sarcoglycan, an interferon, insulin-like growth factor, and erythopoietin.

In a preferred embodiment, the gene therapy is delivery of Factor IX to the mammal.

In yet a further aspect, the gene therapy is performed by administering a viral vector to the mammal, wherein the viral vector comprises a nucleic acid to be delivered to the human. Preferably, the viral vector is an adeno-associated viral vector.

Also preferably, the Factor IX is delivered to the mammal using an adeno-associated virus vector.

In another aspect, the immunosuppressive agent is selected from the group consisting of cyclophosphamide, FK506, anti-CD40 ligand, CTLA4Ig, cyclosporin, antiB71-B72, and an immunosuppressive steroid.

In a preferred embodiment, the immunosuppressive agent is cyclophosphamide.

In another preferred embodiment, the immunosuppressive agent is FK506.

In a further preferred embodiment, the mammal has hemophilia B and the inhibitory antibodies specifically bind with Factor IX protein.

BRIEF DESCRIPTION OF THE DRAWINGS

FIG. 2, comprising FIG. 2A depicts aPTT values and indicates that the mice never exhibited correction of the aPTT. FIG. 2B depicts Bethesda titers and indicates that inhibitory antibodies were still present even when the anti-CD40 ligand was co-administered to the animals.

FIG. 4, comprising FIGS. 4A-4E, is a series of images of the results of Western blotting experiments depicting antibody to murine F.IX in hemophilic mice injected with AAV-mF.IX.

DETAILED DESCRIPTION OF THE INVENTION

Figure 1:
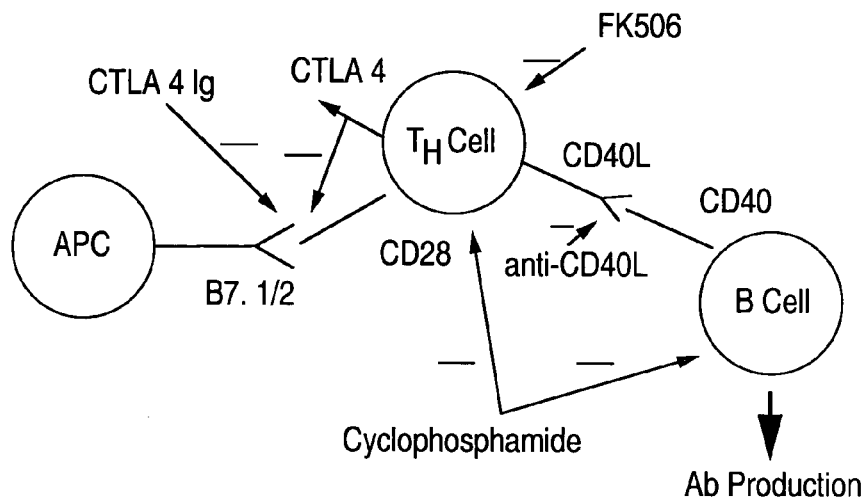
FIG. 1 is a diagram demonstrating sites of action of various immunomodulatory agents within the immune system. APC stands for antigen presenting cell.

The invention relates to the discovery of a method of preventing the formation of inhibitory antibodies to blood clotting proteins in a mammal administered the proteins in a gene therapy protocol. The most serious complication of protein-based therapy for hemophilia is the formation of inhibitory antibodies to blood clotting factors. These antibodies are also induced in the context of gene based therapy for hemophilia. The invention provides a method of preventing the formation of inhibitory antibodies in the setting of gene therapy for hemophilia, wherein the method comprises administration to a mammal undergoing gene therapy an immunosuppressive agent to the mammal.

The gene therapy methods for which the present invention is applicable are described in International Application PCT/US98/04790 which is hereby incorporated herein by reference in its entirety. As such these methods are not exhaustively repeated in the present application. Moreover, such technology is now well known in the art being described, for example, in Herzog et al., 1997, Proc. Natl. Acad. Sci. USA 94: 5804-5809; Herzog et al., 1999, Nature Medicine 5:56-63; Herzog and High, 1999, AAV-mediated gene transfer of factor IX for treatment of hemophilia B by gene therapy. In: Thrombosis and Haemostasis, 1999 State of the Art, Hoyer L (ed.), 82:540-546. Matsushita et al., 1998, Gene Ther. 5:938-945; Matsushita et al., 1999, Improvements in AAV vector production: Elimination of pseudo-wild type AAV. Proceedings of the 2nd annual American Society of Gene Therapy, Washington, D.C., June 9-13, p. 2a; Nakai et al., 1998, Blood 91:4600-4607.

DEFINITIONS

The articles "a" and "an" are used herein to refer to one or to more than one (i.e. to at least one) of the grammatical object of the article. By way of example, "an element" means one element or more than one element. APlurality≡means at least two.

As used herein, "treating a disease" means reducing the frequency with which a symptom of the disease is experienced by a patient.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules.

By the term "inhibitory antibody" as used herein is meant an antibody which specifically binds to a protein expressed in a mammal, which protein has been delivered to the mammal by way of gene therapy.

By the term "specifically binds," as used herein, is meant an antibody which recognizes and binds a specific protein in a sample, but does not substantially recognize or bind other molecules in the sample.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Immunosuppressive agent," refers to a compound which is capable of suppressing the immune response in a mammal. Preferably, the immunosuppressive agent exerts an effect in the mammal which results in a reduced ability of the mammal to generate antibodies directed against a desired protein, specifically a protein delivered to the mammal in a gene therapy protocol.

"Gene therapy," refers to the process of correcting a genetic defect in a mammal comprising administering to the mammal a nucleic acid, which when expressed in the mammal, produces a protein which serves to correct the defect. The process also refers to the administration of a nucleic acid to a mammal where the administered nucleic acid serves to correct a genetic defect in the mammal whether or not a protein is expressed by the administered nucleic acid, i.e., for example, the process of DNA repair.

A "gene therapy based protocol" is a protocol in which gene therapy is accomplished.

The Invention

The invention includes a method of preventing the formation of inhibitory antibodies in a mammal undergoing gene therapy wherein the method comprises administering to the mammal an immunosuppressive agent in conjunction with the gene therapy. As noted elsewhere herein, gene therapy typically involves delivery of a vector to a mammal, wherein the vector comprises an expressible DNA encoding a desired protein. When the vector is delivered to the mammal and the protein is expressed therein, a beneficial effect is experienced by the mammal. However, in certain instances, the immune system of the mammal reacts to the presence of the expressed protein and mounts an antibody response thereto through the production of an inhibitory antibody. Thus, with time, or even immediately, the gene therapy is rendered ineffective because the inhibitory antibody specifically binds to the delivered protein rendering the protein incapable of exerting the desired beneficial effect to the mammal. Administration of the immunosuppressive agent to the mammal serves to diminish or ablate the generation of inhibitory antibodies which specifically bind to the protein so delivered.

It is not necessary in the method of the invention that the immunosuppressive agent completely block the production of inhibitory antibodies in the mammal. Rather, in some instances it may be sufficient that the immunosuppressive agent simply reduce the amount of antibody which would normally be produced in the absence of administration of the immunosuppressive agent.

While preferred embodiments of the invention are described herein, it is important to note that the invention should not be construed to be limited to these embodiments. Rather, the invention should be construed to include the use of an immunosuppressive agent in any type of gene therapy.

In one preferred embodiment, the mammal is a human.

In another preferred embodiment, the gene therapy vector is AAV. However, the invention should not be construed as being limited to this vector. Rather, other suitable vectors which are known in the art, or are as yet unknown, may be useful in the methods of the invention.

In yet another preferred embodiment, the mammal is administered Factor IX (F.IX) in a gene therapy based protocol. However, the invention should not be construed to be limited to gene therapy using F.IX. Rather, the invention should be construed to include the delivery of any protein to a mammal via a gene therapy based protocol. Examples of proteins suitable for delivery include, but are not limited to, any other blood coagulation protein, including, but not limited to, Factor VII, Factor VIII, Factor X, proteins such as alpha1-antitrypsinogen, glucuronidase, sarcoglycans, interferons, insulin-like growth factor, and erythopoietins.

In the method of the invention, the immunosuppressive agent is administered to the mammal prior to, and/or concomitantly with, and/or following administration of the gene therapy vector to the mammal. Depending on the type of gene therapy and the type of immunosuppressive agent being used, it may be necessary to vary the time at which the immunosuppressive agent is administered to the mammal relative to the administration of the therapy itself. One of skill in the art of gene therapy and immunosuppression will know, based on the present disclosure, the state of the art, the type of therapy and immunosuppressive agent and the status of the mammal, how to design a successful protocol with undue experimentation.

A preferred immunosuppressive agent in the present invention is cyclophosphamide. However, the invention should not be construed to be limited solely to the use of this immunosuppressive agent. Rather, the invention should be construed to include any and all suitable immunosuppressive agents which are presently known or which become known. Examples of currently known immunosuppressive agents suitable for use in the present invention include, without limitation, cyclophosphamide, FK506, anti-CD40 ligand, CTLA4Ig, cyclosporin, antiB71-B72, and immunosuppressive steroids.

In a preferred embodiment, and when the gene therapy vector comprises an AAV vector containing DNA encoding F.IX, the immunosuppressive agent is cyclophosphamide.

In another preferred embodiment, the mammal is concomitantly administered about four doses of cyclophosphamide. As disclosed elsewhere herein, such an administration protocol results in the prevention of formation of inhibitory antibodies against F.IX in mice having hemophilia B. The type of hemophilia in the mice used in the present study is the result of the fact that the genome of the mice comprises a large deletion in the gene encoding F.IX; such a genetic defect generally results in a high likelihood of inhibitor formation. Co-administration of cyclophosphamide with a gene therapy vector comprising the F.IX gene, greatly lessened or abolished this undesirable side effect.

Kay et al. (1997, Proc. Natl. Acad. Sci. USA 94:4586-4691) have described the use of other immunomodulatory agents to block the immune response to a gene therapy vector; however, this disclosure does not teach the use of immunosuppressive agents for the purpose of inhibiting antibody development directed against the delivered protein. The present invention is specifically directed to inhibition of the generation of antibody specific for the therapeutic gene product itself. The use of immunosuppressive regimens to prevent the formation of inhibitors once they have occurred in the setting of protein-based therapy has been described. Results have been mixed and this treatment modality is not universally used.

The present invention provides a unique solution to the problem of inhibitor formation which is directed against the gene therapy based delivered protein because it works in the setting of gene therapy; and the success rate of the method is high, even when the genetic defect being corrected (large gene deletion) is most likely to result in the generation of inhibitory antibodies directed against the delivered protein. Thus, the method of the present invention solves the most critical problem in gene therapy for hemophilia, i.e. it prevents the formation of inhibitory antibodies.

The preferred method of the invention comprises the administration of cyclophosphamide concomitantly with the administration of a gene therapy vector for the purpose of alleviating hemophilia. Cyclophosphamide is given in about four doses each having a concentration of about 50 mg/kg of body weight per mammal. The compound may be administered intravenously or intraperitoneally. Alternatively, an equivalent per oral administration (PO) dose can be given.

However, other dosages and routes of administration are also contemplated, in that, cyclophosphamide may be administered at a lower dose of, for example, 20 mg/kg of body weight, and/or fewer doses may be administered to the mammal. The amount of dosage will depend on the type of mammal being treated and on the level of gene therapy required to alleviate the disease state in the mammal.

The amount of dosage of any immunosuppressive agent can be determined empirically by the skilled artisan, and will depend on any number of factors known to the artisan, including, but not limited to, the factors mentioned elsewhere herein, for example, the type of immunosuppressive agent used, the nature of the disease being treated, the type of vector and protein used, the overall health of the mammal, gender, the age of the mammal, etc. It is sufficient for the present disclosure that examples of successful protocols be provided to guide the artisan.

When the protocol involves the administration of four doses of cyclophosphamide, and the gene therapy being performed is delivery of an AAV vector comprising F.IX DNA, the first dose of cyclophosphamide is administered within twenty four hours of treatment with the gene therapy vector, and subsequent doses are administered at two week intervals. In the experiments disclosed herein in the Example, in mice that received this regimen, 3/3 animals exhibited no evidence of inhibitor antibody formation during the period post-administration of the gene therapy vector for as long as at least five months. These data are summarized in detail in the experimental details provided herein.

As noted previously, the invention should in no way be construed as being limited solely to the use of cyclophosphamide, or to the dosages, routes of administration and dose regimens disclosed herein. Rather, the invention should be construed to encompass the use of immunosuppressive agents in conjunction with the administration of a gene therapy vector, wherein the vector is administered to the mammal for the purpose of delivering a protein to a mammal, and the immunosuppressive agent is administered to the mammal for the purpose of preventing the formation of inhibitory antibodies to the delivered protein.

The invention is thus useful for the prevention of inhibitory antibody formation in mammals, including humans, undergoing gene therapy treatment for hemophilia. The major therapeutic benefit of the method of the invention is the prevention of formation of inhibitory antibodies to the transgene product, i.e., to the delivered protein, exemplified herein as a coagulation factor. In addition, transient immunosuppression at the time of vector administration may allow re-administration of the vector to the mammal thereby achieving a higher level of efficacy than would be possible without concomitant transient immunosuppression.

The invention is now described with reference to the following experimental examples. These examples are provided for the purpose of illustration only and the invention should in no way be construed as being limited to these examples but rather should be construed to encompass any and all variations which become evident as a result of the teaching provided herein.

EXAMPLES

In a gene based setting the production of a secretable protein in a host animal that has no endogenous expression of the gene may lead to an immune response to the transgene product. In patients with severe hemophilia B inhibitor formation in response to infusion of coagulation Factor IX (F.IX) concentrate occurs in about 4% of patients. One of the main determinants of inhibitor formation is the genotype of the underlying mutation; in general the greater the loss of coding information the more likely the development of an inhibitory antibody. The risk of inhibitor development is not well understood in the context of a gene therapy approach to hemophilia B.

In the experiments described herein, the prevalence of inhibitor development in a murine model of hemophilia which is caused by a large deletion affecting the promoter region and exons 1-3 of the F.IX gene (Lin et al., 1997, A Coagulation Factor IX-Deficient Mouse Model for Human Hemophilia B, Blood, 90:3962-3966) was assessed. This results in an absence of F.IX transcript and protein. The second aim of the study was to evaluate the effect of immunomodulation in reducing the risk of inhibitor development.

A cohort of six mice were injected intramuscularly with an adeno-associated virus (AAV) vector encoding the murine F.IX transgene (total dose $1\times10^{11}$ vector genomes/mouse). Mice were bled at monthly intervals via tail vein transection, and clotting times of plasma were measured by aPTT assay. None of the mice exhibited correction of the aPTT (59.9-709 s; normal values 22-39 second) compared with pretreatment values (53.6-66.9 s). Bethesda titers revealed evidence of inhibitory activity in all mice by one month which rose on further testing at two months (see Table below). Antibodies were also detectable on Western Blot, although there was individual variation in temporal appearance and titer. Two other cohorts of mice received immunomodulation around the time of vector administration in an effort to suppress inhibitor formation. One cohort (n=4) received anti-CD40L antibody at a total dose of 0.4 mg per mouse given in four divided doses (0.1 mg at days -3, 0, 3, 6) while the other cohort received cyclophosphamide (CYP, n=4) at doses of 50 mg/kg per mouse biweekly at four time points. CD40L antibody-treated mice exhibited partial correction of the aPTT (46.4-57.4 s). In the CYP-treated mice, nearly complete correction of the aPTT was observed (28.9-30.9 s) in all mice at one month and this has been maintained for the study period of greater than ten months. These data correlate with reduction or absence of inhibitor formation in immunosuppressed animals. This study provides evidence of successful suppression of inhibitor formation with immune modulation in a muscle-directed gene therapy for treatment of hemophilia B.

TABLE

| Bethesda titer of AAV-F.IX treated mice | | |
|---|---|---|
| Months | 1 | 2 |
| no immunosuppression | 2.8//0.9/3/3.5 | 4.3/16/16/2.4 |
| CYP | 0/0/0 | 0/0/0 |
| anti-CD4OL | 0/1.3/0/0 | 0/0/7 |

The methods used in these experiments include the following:

Hemophilia B knockout mice were injected intramuscularly with AAV mF.IX ($1\times10^{11}$) at day 0, without or with immunomodulation therapy. The mice were bled at monthly time points in citrate. The assays which were performed included a clotting based-apTT (measure of correction of hemostatic defect) assay and Bethesda titer (1 BU defined as 50% residual FIX in a 2 hour 50:50 mix). In addition, antibody assays, Western blot analysis and ELISA assays were performed. The immunomodulatory strategies used to address formation of antibodies to the transgene product were as follows:

CD40L antibody—0.1 mg intraperitoneally at day -3, day 0, day +3, day +6, day +9;

Cyclosporin A—100 mg/kg intraperitoneally three times weekly;

Cyclophosphamide—50 mg/kg intraperitoneally at day 0, week 2, week 4, week 6;

FK506—125 µg subcutaneously on alternate days from day 0.

The Results of the experiments presented in this example are now described in conjunction with Figures which illustrate these results.

FIG. 1 is a diagram demonstrating sites of action of various immunomodulatory agents within the immune system. APC stands for antigen presenting cell.

Control mice were injected with AAV-mF.IX at day 0. aPTT values were measured and graphed as a function of time after injection. The aPTTs remained constant throughout the duration of the experiment, indicating that no correction of clotting time had occurred. The Bethesda titers, a measure of inhibitory antibody titer, were also assessed as a function of time. These values were high throughout the course of the experiment.

Figure 2A:
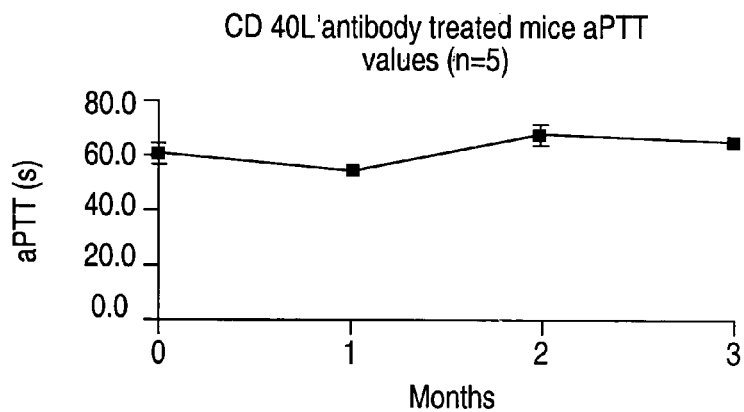
FIGS. 2A and 2B, is a series of graphs illustrating the data obtained when the mice received anti-CD40 ligand (anti-CD40L) as well as AAV-mF.IX.
Figure 2B:
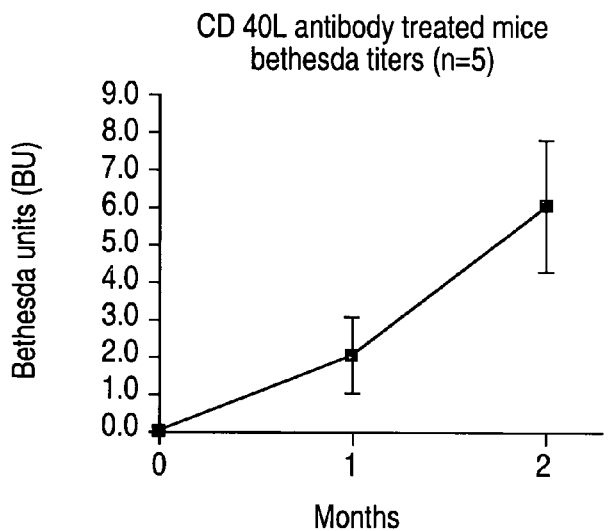

In FIG. 2 there is shown the data obtained when the mice received anti-CD40L as well as AAV-mF.IX. The panel on the left comprises aPTT values and indicates that the mice never exhibited correction of the aPTT. The panel on the right comprises Bethesda titers and indicates that inhibitory antibodies were still present even when the anti-CD40 ligand was co-administered to the animals.

Figure 3:
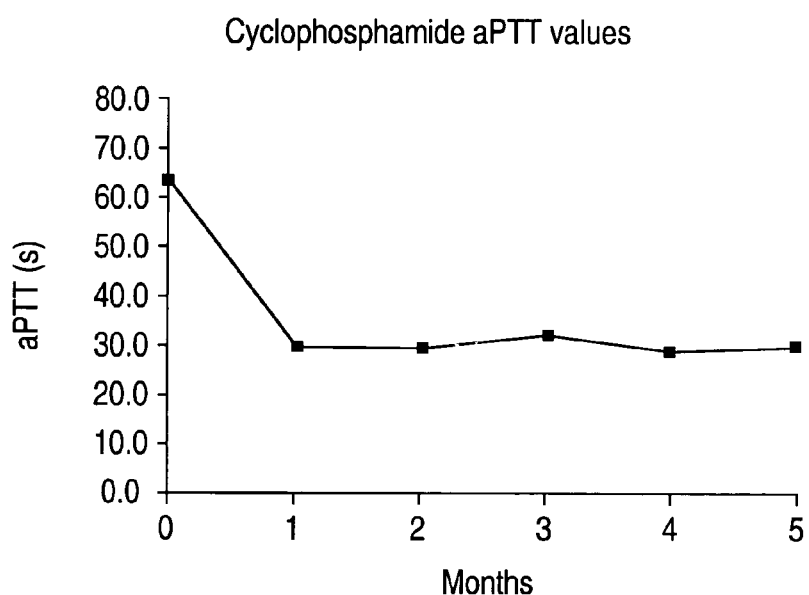
FIG. 3 is a graph depicting aPTT values obtained from mice treated with cyclophosphamide at the time of AAV-mF.IX vector administration.

In FIG. 3 there is shown aPTT values obtained from mice treated with cyclophosphamide at the time of AAV-mF.IX vector administration. In contrast to the previous data, these mice exhibited sustained correction of the aPTT, indicating that inhibitory antibodies never formed in these animals. This remained the case at five months after the original vector injection and fourteen weeks after the last doses of cyclophosphamide was administered.

In FIG. 4 there is shown the results of a Western blot depicting antibody to murine F.IX in hemophilic mice injected with AAV-mF.IX. Both the control mice and the anti-CD40 ligand treated mice developed antibodies one month after vector injection, but the cyclophosphamide treated mice did not develop antibodies through the five months of observation.

Figure 5:
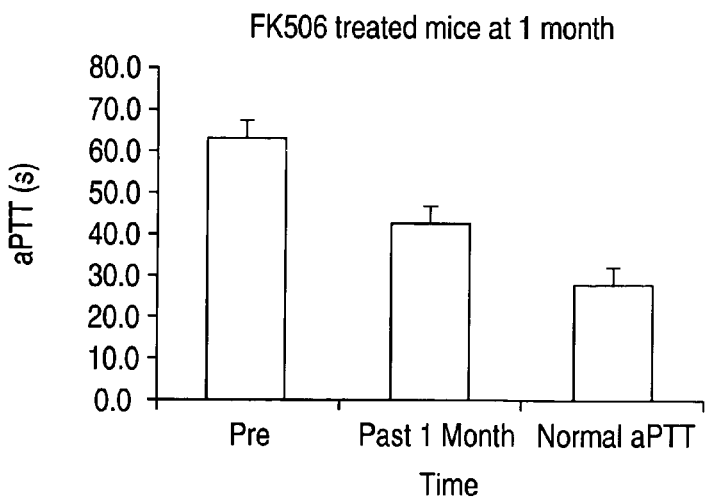
FIG. 5 is a graph illustrating data which establish that the immunosuppressive agent, FK506, is useful for the prevention of formation of inhibitory antibodies, in that, mice treated with FK506 exhibited shorter aPTT coagulation times than mice which were not treated with FK506.

In FIG. 5 there is shown data which establish that the immunosuppressive agent, FK506, is useful for the prevention of formation of inhibitory antibodies, in that, mice treated with FK506 exhibited shorter aPTT coagulation times than mice which were not treated with FK506.

The data presented herein therefore establish that in a murine knockout model of hemophilia B (large gene deletion) all mice injected with AAV mFIX made antibodies which are inhibitory to the transgene product. The antibodies are of a lgG 1 subclass which is in keeping with a $T_{H2}$ response. Antibody formation to the transgene product may be decreased by transient immune suppression at the time of vector administration resulting in correction (or partial correction) of the hemostatic defect. The immunosuppressive agents, cyclophosphamide and FK506, are thus useful for inhibition of the generation of inhibitory antibodies directed against a desired protein in mammals receiving gene therapy.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of preventing the formation of inhibitory antibodies to Factor IX delivered to a mammal by way of an adeno-associated viral vector, said mammal showing symptoms of hemophilia B and having a genetic defect which can result in generation of inhibitory antibodies to Factor IX upon administration of exogenous Factor IX, said method comprising
   (a) intravenously or intraperitoneally administering to said mammal an immunosuppressant consisting of cyclophosphamide, and
   (b) delivering Factor IX to said mammal by way of an adeno-associated viral vector, either concomitantly with or following step (a),
   wherein the delivered Factor IX is from the same species as said mammal.

2. The method of claim 1, wherein said mammal is human.

3. The method of claim 1, wherein said cyclophosphamide is administered concomitantly with said adeno-associated viral vector.

4. The method of claim 1, wherein said adeno-associated viral vector is delivered intramuscularly.

* * * * *